US00PP36729P2

(12) United States Plant Patent
Plocher

(10) Patent No.: US PP36,729 P2
(45) Date of Patent: Jun. 10, 2025

(54) GRAPE PLANT NAMED 'Resilience'

(50) Latin Name: ***Vitis* interspecific hybrid**
Varietal Denomination: Resilience

(71) Applicant: Thomas Alan Plocher, Hugo, MN (US)

(72) Inventor: Thomas Alan Plocher, Hugo, MN (US)

( * ) Notice: Subject to any disclaimer, the term of this patent is extended or adjusted under 35 U.S.C. 154(b) by 0 days.

(21) Appl. No.: 19/054,476

(22) Filed: Feb. 14, 2025

(51) Int. Cl.
*A01H 6/88* (2018.01)
*A01H 5/08* (2018.01)

(52) U.S. Cl.
USPC ..... Plt./206
CPC ..... *A01H 6/88* (2018.05); *A01H 5/08* (2013.01)

(58) Field of Classification Search
USPC ..... Plt./206
CPC ..... A01H 6/88; A01H 5/08
See application file for complete search history.

*Primary Examiner* — Keith O. Robinson
(74) *Attorney, Agent, or Firm* — Michelle Bos Legal LLC

(57) ABSTRACT

'Resilience' is a cold-hardy grape plant notable for its large fruit cluster size and its thick-skinned fruit resistant to splitting, insect attack and rot. 'Resilience' grapes are used in the production of wine.

9 Drawing Sheets

Latin name: *Vitis* interspecific hybrid.
Variety denomination: 'Resilience'.

BACKGROUND OF THE VARIETY

'Resilience' is a new and distinct variety of grape plant selected from a group of seedlings obtained from a controlled cross of female parent 'E.S. 10-18-06' (not patented) and male parent 'Regent' (not patented) carried out at Hugo, Minnesota in 2000. Originally designated 'TP 2-3-51', seedling 'Resilience' was selected for further observation in 2007 and was first asexually propagated by dormant hardwood cuttings in 2008 at Hugo, Minnesota; subsequent asexual propagations have shown the variety to be stable and to reproduce true to type through successive generations.

SUMMARY OF THE VARIETY

'Resilience' is a cold-hardy grape plant notable for its large fruit cluster size and its thick-skinned fruit resistant to splitting, insect attack and rot. 'Resilience' grapes are used in the production of wine. A comparison of the 'Resilience' grape plant to its parents is shown in Table 1 below.

TABLE 1

Comparison of 'Resilience' to Parent Varieties

| | 'Resilience' | 'E.S. 10-18-06' | 'Regent' |
|---|---|---|---|
| Winter hardiness | Primary bud hardiness to −29° C. | Primary bud hardiness to −40° C. | Primary bud hardiness to −23° C. |
| Budbreak | Later than 'E.S. 10-18-06'; similar to Regent | Earlier | Similar |
| Acidity at harvest | 0.8% | 1.2% | 0.7% |
| pH | 3.3-3.4 | 3.1-3.2 | 3.5 |
| Vigor | Somewhat less vigorous than 'E.S. 10-18-06'; similar vigor to Regent | slightly more vigorous | Similar |

TABLE 1-continued

Comparison of 'Resilience' to Parent Varieties

| | 'Resilience' | 'E.S. 10-18-06' | 'Regent' |
|---|---|---|---|
| Skin tannins | Higher concentration than 'E.S. 10-18-06'; similar concentration to Regent | Lower | Similar |
| Berry size | 14 mm to 18 mm | 13 mm to 14 mm | 15 mm |
| Cluster size | 194 g | 150 g | 130 g |

A comparison of 'Resilience' to 'Crimson Pearl' (U.S. Plant Pat. No. 30,263), a related cold-hardy variety, is shown in Table 2 below.

TABLE 2

Comparison of 'Resilience' to 'Crimson Pearl'

| | 'Resilience' | 'Crimson Pearl' |
|---|---|---|
| Winter hardiness | Hardy to −29° C. | Hardy to −32° C. to −35° C. |
| Budbreak | Slightly earlier | Slightly later |
| Vigor | Moderate | Moderate |
| Cluster weight | 194 g | 110 g |
| Shoot Angle from cane | 70% (more upright) | 50% (less upright) |
| Acidity at harvest | 0.8% | 0.7% |
| Skin tannins | Higher concentration | Lower concentration |
| Skin thickness | Thicker | Thinner |
| Harvest | 7 days Earlier | 7 days Later |

BRIEF DESCRIPTION OF THE PHOTOGRAPHS

The attached photographs show selected characteristics of 'Resilience' grape plants planted in 2008 and grown on their own roots at Hugo, Minnesota.

Figure 1:
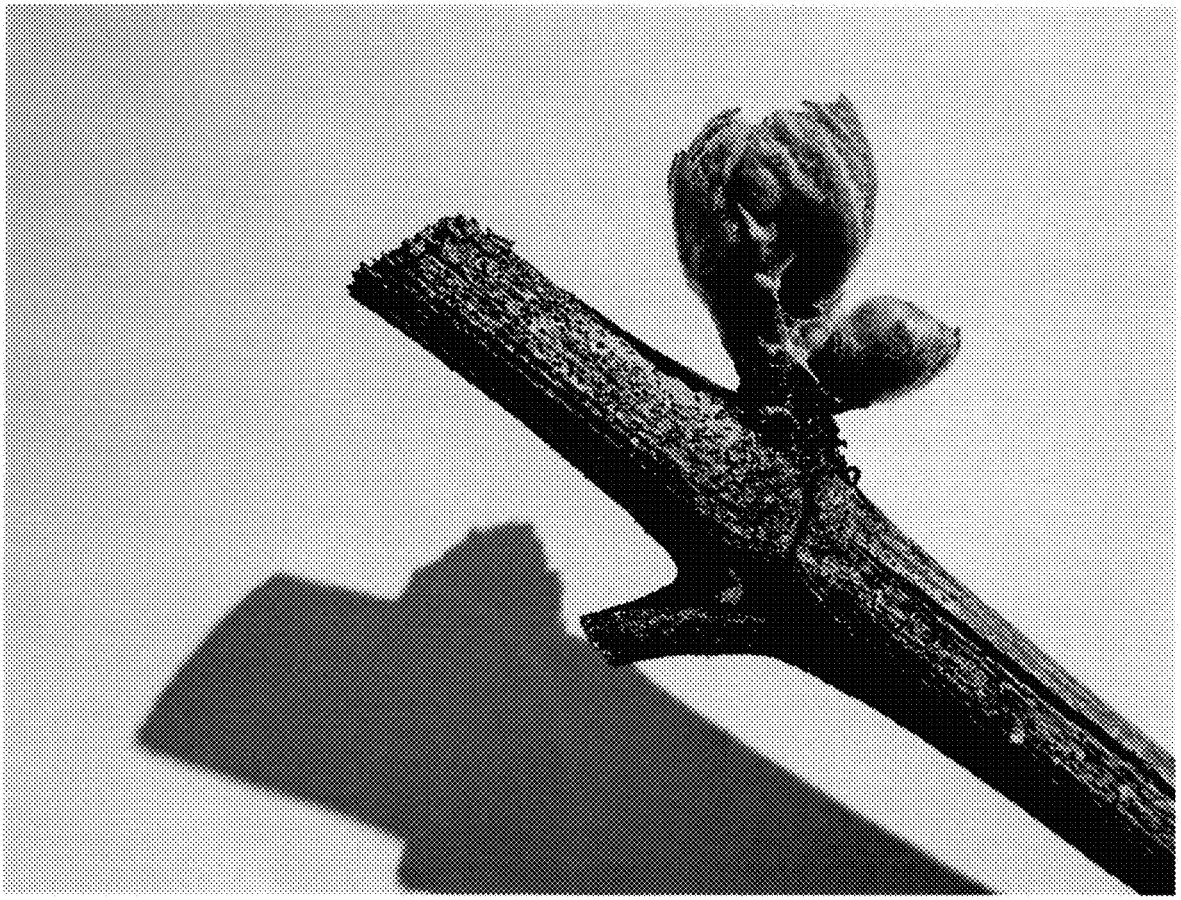
Figure 2:
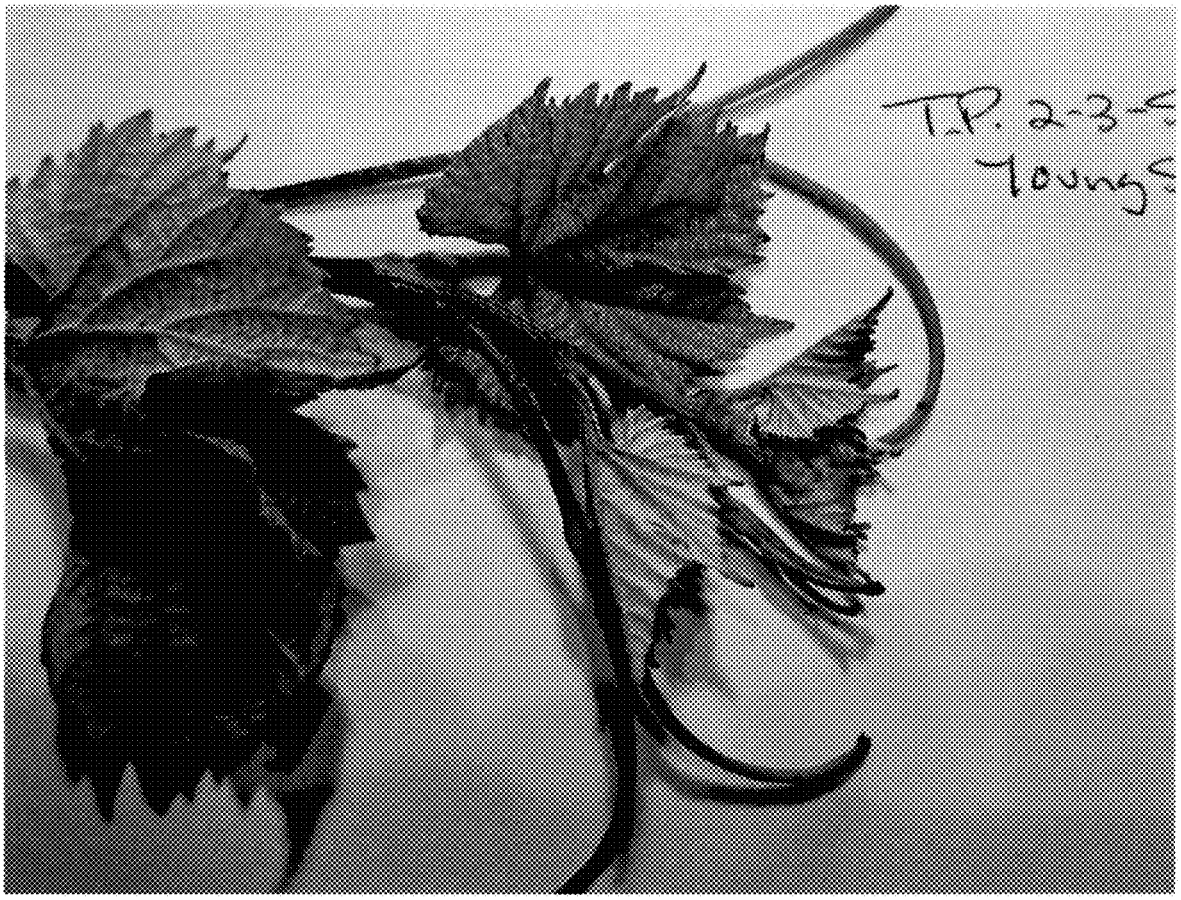
Figure 3:
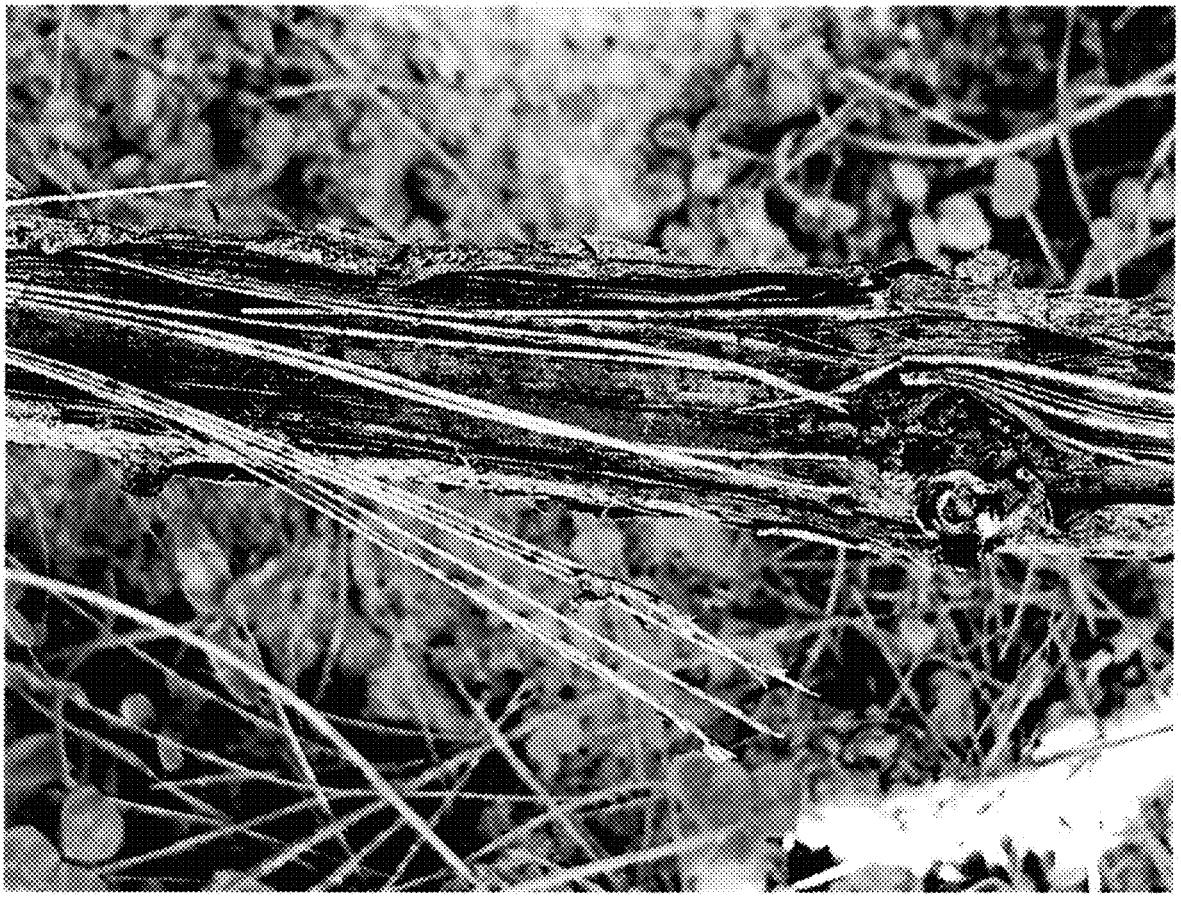

FIG. 1 shows a bud at full burst (2019);
FIG. 2 shows a young shoot and leaves (2019);
FIG. 3 shows the trunk and bark (2019)

Figure 4:
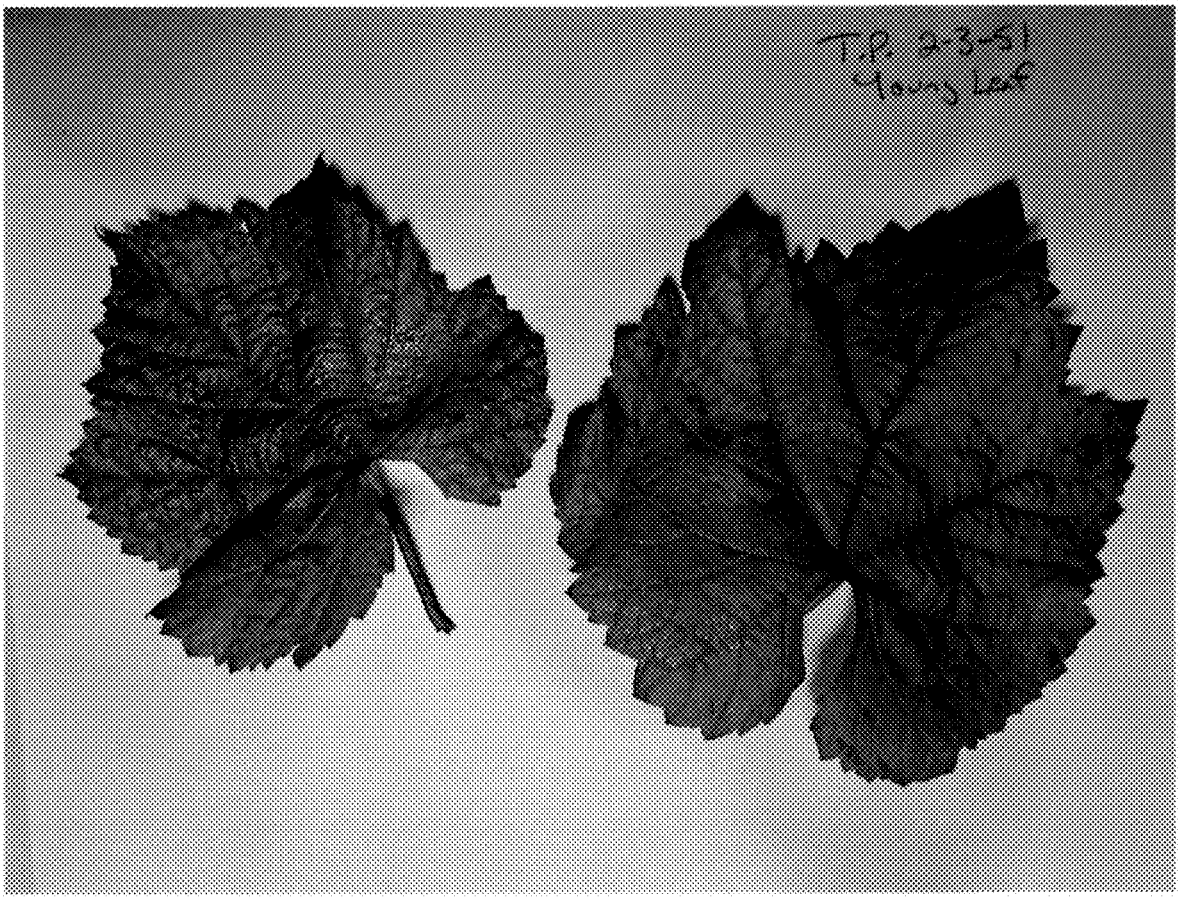
Figure 5:
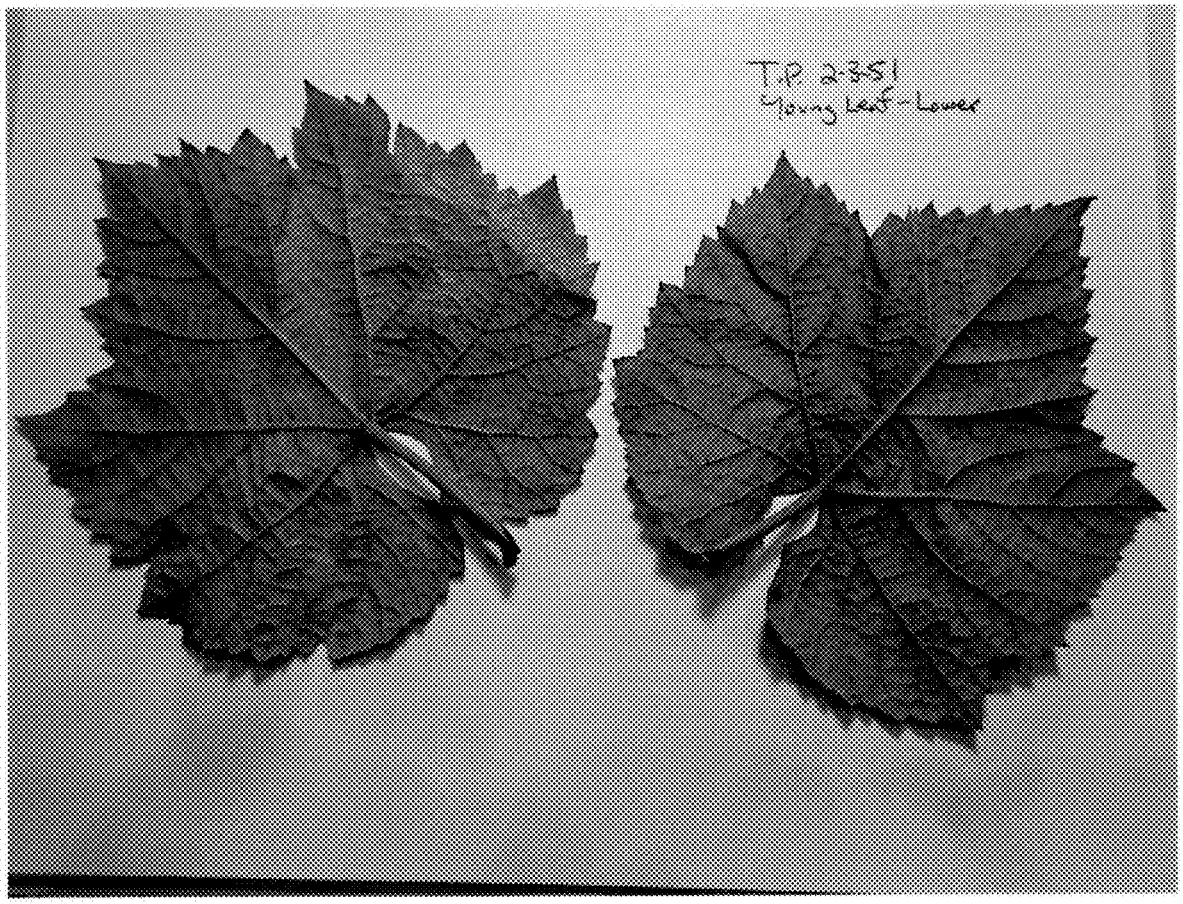
Figure 6:
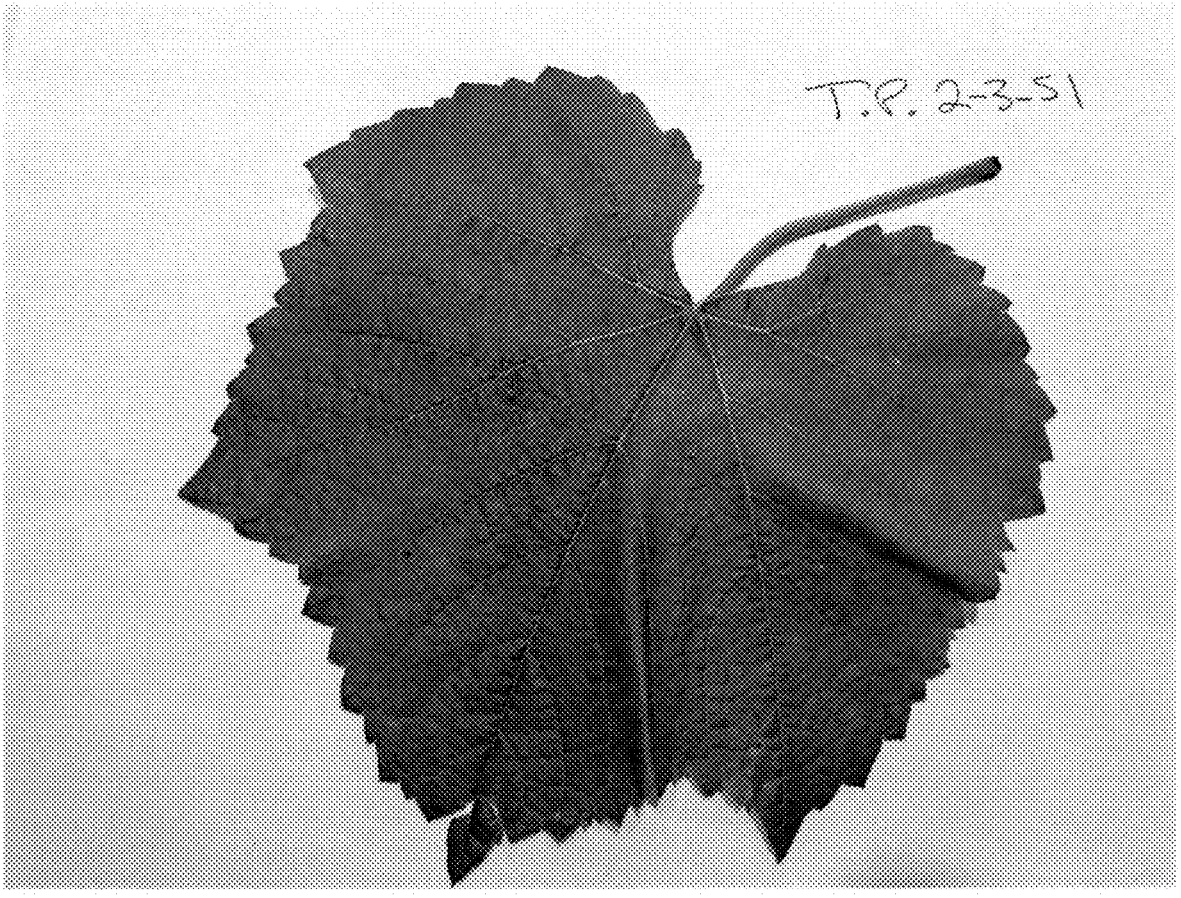
Figure 7:
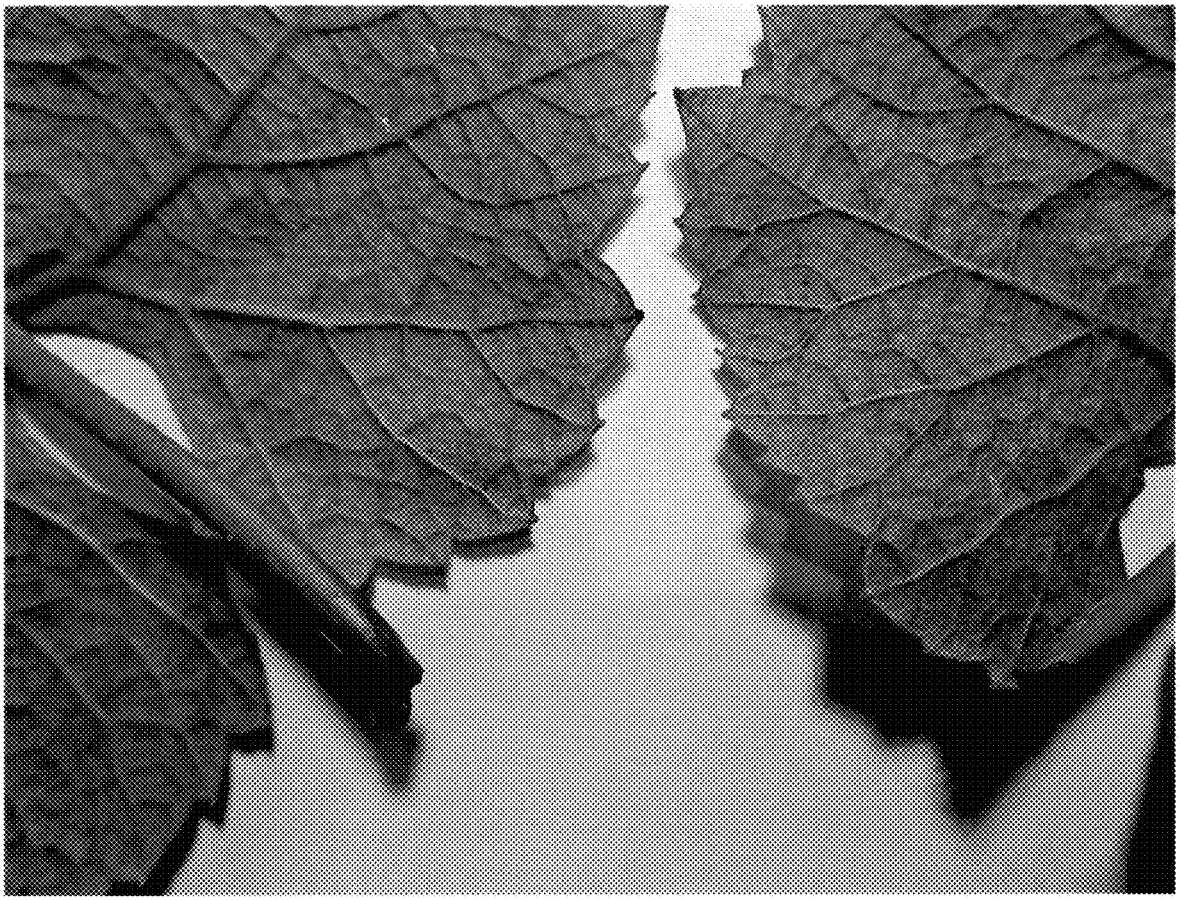
Figure 8:
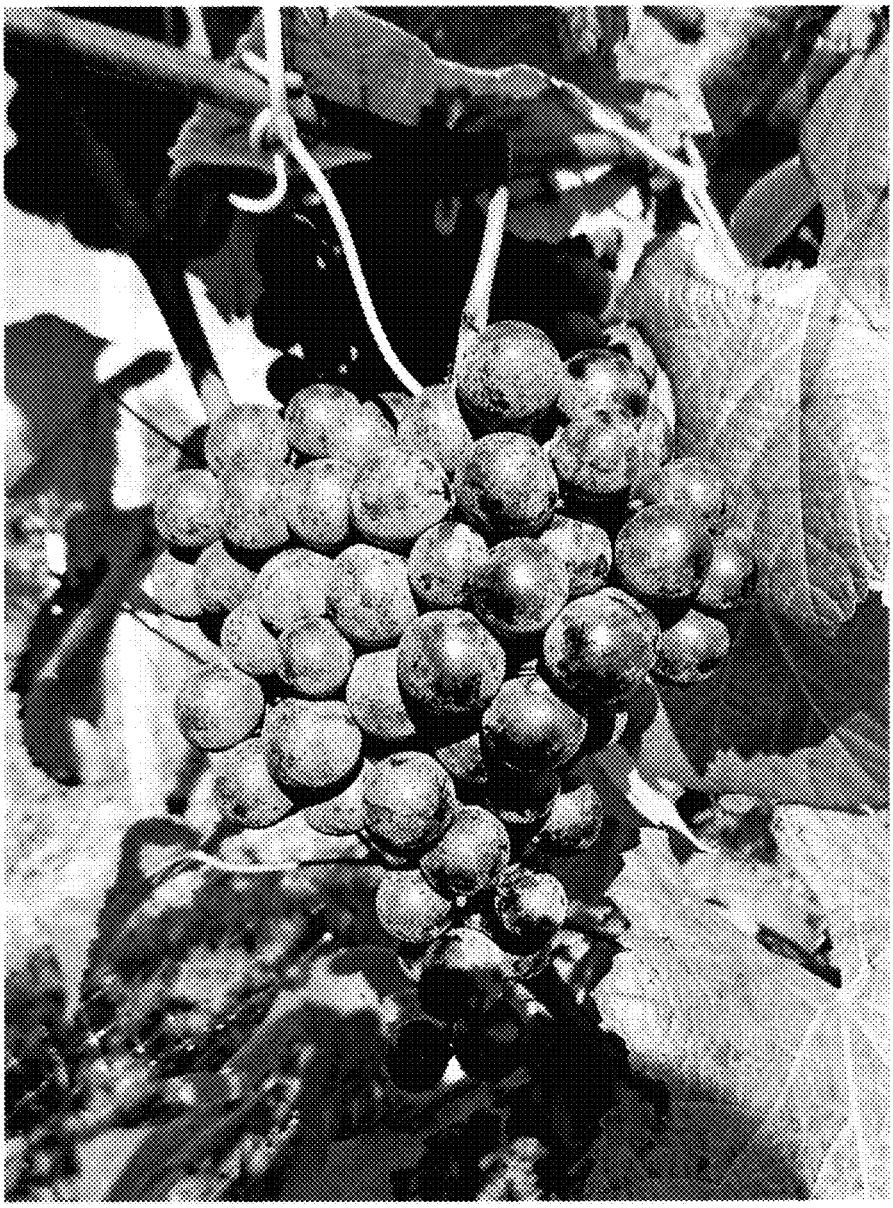
Figure 9:
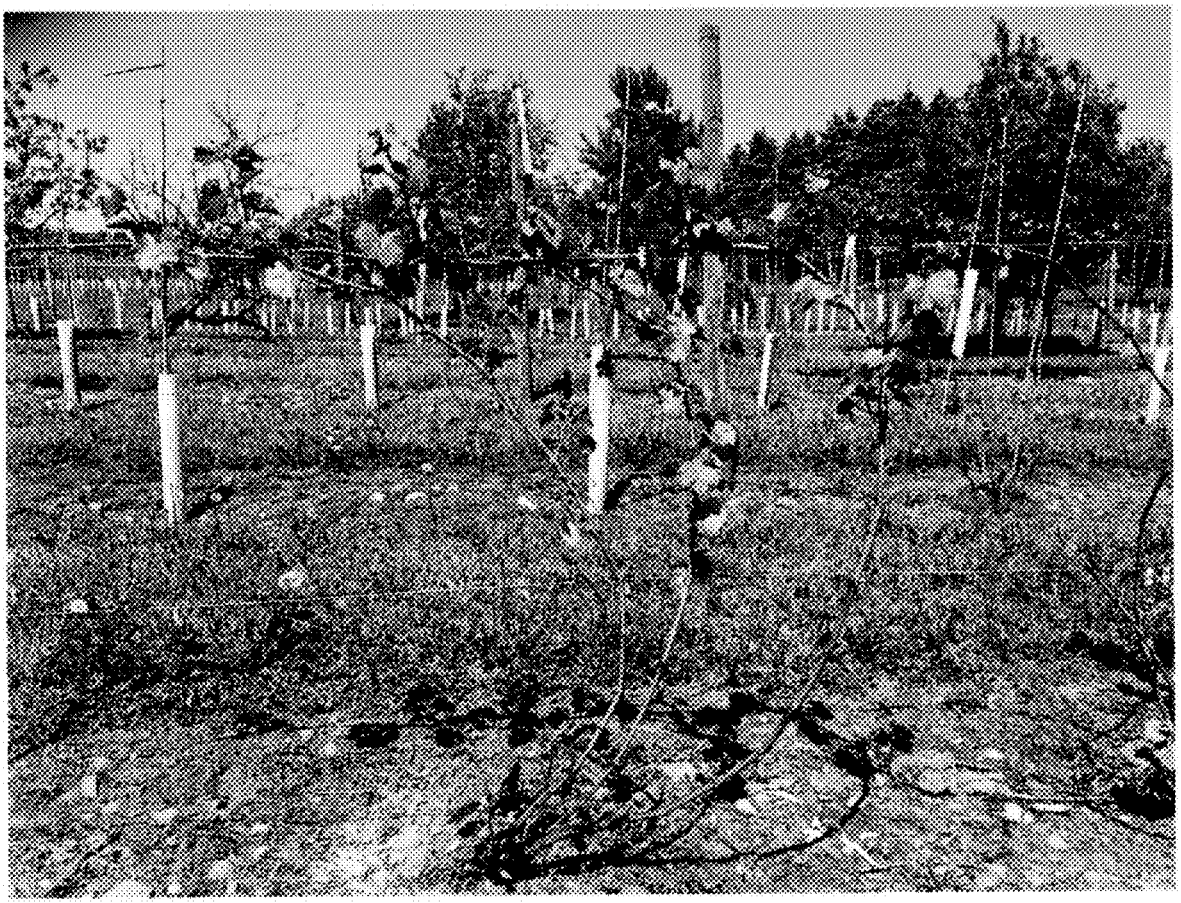

FIG. 4 shows the upper surface of young leaves (2018);
FIG. 5 shows the lower surface of young leaves (2018);
FIG. 6 shows the upper surface of a mature leaf (2016);
FIG. 7 shows the lower surface of a mature leaf (2016);
FIG. 8 shows the canes, leaves, and fruit (2016); and,
FIG. 9 shows the plant growing on a vineyard trellis (2019).

DETAILED BOTANICAL DESCRIPTION OF THE VARIETY

The following detailed botanical description is based on observations made during the 2016, 2018 and 2019 growing seasons. The plants were planted in 2008 at Hugo, Minnesota. All colors are described according to The R.H.S. Colour Chart (6th edition). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. "Degree Days Fahrenheit Base 50" ("DDF 50") refers to accumulated heat units.

Vine:
- *Size*.—Medium.
- *Form*.—Thick shoots with fairly strong upright growth habit.
- *Vigor*.—Moderate.
- *Timing of bud burst*.—5 May 2018 (100% first swell stage at 90.2 DDF 50).
- *Productivity*.—3 to 4 tons per acre on average soil.
- *Trunk diameter*.—1.8 cm at about 5 cm above the ground on 2-year-old trunks.
- *Bark texture*.—Rough and slightly exfoliating.
- *Bark color*.—Dark Greyish Yellowish Brown N200B.

Canes:
- *Diameter*.—8.8 mm.
- *Quantity*.—Typically 30 canes.
- *Bark color*.—Overwintered canes Dark Reddish Orange 175C with very thin (0.2 mm) longitudinal lines of Dark Greyish Reddish Brown 200A and Light Brownish Grey mottling N200C.
- *Bark texture*.—Smooth.
- *Form*.—Round in cross section.
- *Node size*.—15.1 mm.
- *Internode length*.—11.5 cm.
- *Number of tendrils per node*.—Regular repeating pattern of 2 consecutive nodes with tendrils followed by 1 or 2 nodes without tendrils.
- Tendril diameter.—2 mm to 3 mm.
- *Tendril length*.—Natural 12.5 cm; stretched 15.3 cm.
- *Tendril texture*.—Smooth.
- *Tendril color*.—Strong Yellow Green 144B, with Dark Purplish Red N79B on one side below the point where the tendril divides into two parts.

Flowers:
- *Fertility*.—Self-fertile.
- *Date of bloom*.—7 Jun. 2016, 50% caps off (approximately 486 DDF 50) from 1 January.
- *Number of inflorescences per shoot*.—2.
- *Numbers of flowers per inflorescence*.—475 to 631.
- *Shape of flower cluster*.—Conical.
- *Length of flower cluster*.—11.2 cm to 13.7 cm.
- *Width of flower cluster*.—5.8 cm to 7.2 cm.
- *Peduncle length*.—2.5 cm to 4.5 cm; Average 3.8 cm.
- *Peduncle diameter*.—2.4 mm to 3.3 mm; Average 2.8 mm.
- *Peduncle color*.—Strong Yellow Green 144B; some faint to notable Dark Purplish Red 59B on one side.
- *Pedicel length*.—2.0 mm to 3.5 mm; Average 1.8 mm.
- *Pedicel diameter*.—0.25 mm to 0.4 mm.
- *Pedicel color*.—Strong Yellow N144B.
- *Flower depth*.—6.6 mm.
- *Flower diameter*.—5.8 mm.
- *Filament length*.—2.8 mm to 3.0 mm; Average 3.4 mm.
- *Filament color*.—Pale Yellow Green 157C.
- *Anther length*.—0.6 mm to 0.7 mm.
- *Anther color*.—Light Yellow 11B.
- *Pistil length*.—2.5 mm to 2.6 mm.
- *Pistil color*.—Strong Yellow Green N144C.
- *Stamen color*.—Pale Yellow Green 157C.
- *Stamen length*.—2.8 mm to 3.0 mm.
- *Stamen quantity*.—5.
- *Cap color*.—Strong yellow green 144B; about 80% of the caps have a small Dark Red 59A marking on top of the cap in the center, ranging from a tiny dot to a tiny star pattern approximately 1 mm in diameter.
- *Flower type*.—Hermaphroditic.

Young shoots:
- *Openness of the tip*.—Closed.
- *Density of prostrate hairs on tip*.—Very dense.
- *Color of prostrate hairs on tip*.—Very Light Purple 76B.

Young leaf:
- *Shape*.—Circular.
- *Length*.—8.5 cm to 14.4 cm; Average 12.4 cm.
- *Width*.—8.3 cm to 14 cm; Average 11.5 cm.
- *Color of upper surface*.—Moderate Yellowish Green 138A with Dark Red 59A anthocyanin pigmentation at the intersection of the petiole with the main leaf veins. In some cases, pigmentation extends for 1 cm along the major and minor veins, and may also occur at the major bifurcations of the main vein into the main lateral veins.
- *Color of lower surface*.—Moderate yellowish green 138A.
- *Density of prostrate hairs between main veins on lower side of blade*.—Very dense.
- *Density of erect hairs on main veins on lower side of blade*.—Low density.
- *Color of young tendril*.—Yellow Green 144B with Dark Purplish Red N79B on one side below the point where the tendril divides into two parts.

Mature leaf:
- *Relative size*.—Medium.
- *Length*.—14.0 cm to 16.5 cm; Average 15.4 cm.
- *Width*.—14.0 cm to 19.0 cm; Average 16.1 cm.
- *Thickness*.—0.44 mm to 0.57 mm; Average 0.48 mm.
- *Shape*.—Wedge-shaped to circular.
- *Margin*.—Erose to serrate.
- *Blistering on upper surface*.—Strong.
- *Texture of upper surface*.—Hairless between veins and highly corrugated; top of veins hairless; sides of veins with moderately dense erect hairs.
- *Texture of lower surface*.—Hairless between veins; dense prostrate hairs on the minor veins and the sides of the major veins; hairs on the minor veins frequently appear in clumps.

*Density of prostrate hairs between main veins on lower side of blade*.—Sparse to none.

*Density of erect hairs on main veins on lower side of blade*.—Few erect hairs.

*Color of upper surface*.—Moderate Yellowish Green 138A.

*Color of lower surface*.—Moderate Yellowish Green 138B.

*Anthocyanin coloration of main veins on upper surface*.—Dark Purplish Red 59B; very slight and confined to the base of the main vein 75% of the extent of the veins.

*Number of lobes*.—5.

*Terminal lobe form*.—Convex on both sides.

*Lateral sinus depth*.—Left: 0.8 cm to 1.5 cm; Average 1.16 cm. Right: 1.0 cm to 1.5 cm; Average 0.96 cm.

*Lateral sinus shape*.—Very shallow asymmetrical V-shape.

*Relative arrangement of lateral sinus lobes*.—Very open.

*Petiole color*.—Strong Yellowish Green 144A with Deep Purplish Red 59B prominent at distal and more dominant on upper side of petiole.

*Petiole sinus depth*.—3.8 cm to 5.2 cm; Average 4.62 cm.

*Petiolar sinus shape*.—Inverted U-shape.

*Relative arrangement of petiolar sinus lobes*.—Varies from narrow and moderately open to touching; in about 10% of leaves the lobes overlap.

*Petiole sinus limited by veins*?.—Yes.

*Petiole length*.—6.4 cm to 11.6 cm; Average 9.19 cm.

*Petiole diameter*.—2.78 mm to 4.39 mm; Average 3.32 mm.

*Length of middle vein*.—8.9 cm to 13 cm; Average 10.44 cm.

*Ratio of petiole length/length of middle vein*.—0.62 to 1.0; Average 0.83.

*Length of teeth*.—0.3 cm to 0.8 cm; Average 0.47 cm.

*Width of teeth*.—0.5 cm to 1.1 cm; Average 0.85 cm.

*Ratio of length/width of teeth*.—0.36 to 1.0; Average 0.57.

Mature tendrils (measured after veraison):

*Quantity*.—Tendrils occur in repeating pattern of 2 consecutive nodes with tendrils followed by 1 or occasionally 2 nodes without tendrils.

*Thickness*.—2 mm to 3 mm.

*Length*.—Natural 12.5 cm; stretched 15.3 cm.

*Texture*.—Smooth.

*Color*.—Strong Yellowish Green N144A with Dark Red 59A on upper side of proximal half of tendril, occasionally extending just beyond the branching point of the tendril.

Shoot (measured at flowering):

*Attitude* (*before tying*).—Tending toward upright growth habit with shoots at 70° angle relative to the cane from which they arise.

*Color of dorsal side of internode* (*well-illuminated*).—Dark Red 59A over Strong Yellow N144B.

*Color of ventral side of internode* (*without direct sunlight*).—Strong Yellow N144B.

*Density of erect hairs on internodes*.—Present but very sparse.

*Number of consecutive tendrils*.—No tendrils up to node 5, then 2 consecutive tendrils followed by no tendril followed by two consecutive tendrils.

*Length of tendrils*.—11 cm to 15 cm; Average 13.2 mm.

*Thickness of tendrils*.—1.4 mm to 1.8 mm; Average 1.6 mm.

*Form of tendril*.—One point of branching into two branches, near middle of tendril.

*Texture of tendril*.—Smooth.

*Color of tendril at flowering*.—Strong Yellow Green 144A with Dark Red 59A mottling on sun side.

Fruit:

*Veraison* (*50% to 70% of berries colored*).—6 Aug. 2016 (1801 DDF 50).

*Maturity date*.—Mid-September in Hugo, MN (45.1600° N, 92.9933° W); 22 Sep. 2016 (2645 DDF 50); 2 days later than 'TP 1-1-12' (U.S. Plant Pat. No. 31,934); 7 days earlier than 'Crimson Pearl'.

*Shape*.—Roundish.

*Length*.—14.57 mm to 17.13 mm; Average 15.74 mm.

*Width*.—15.27 mm to 18.09 mm; Average 16.61 mm.

*Weight*.—2.5 g.

*Relative size*.—Slightly larger than 'Crimson Pearl'.

*Brix*.—20.5 degrees.

*Skin thickness*.—1.32 mm to 1.55 mm; Average 1.44 mm.

*Skin color*.—Grey Purplish Blue 103A overlaid with Light Blue 98C.

*Flesh color*.—Light yellow 160B with heavy streaks of Deep Red 60A.

*Anthocyanin coloration in flesh near seeds*.—Dark Red 59A.

*Flesh texture*.—Slipskin, gelatinous.

*Number of berries per cluster*.—72 to 117; Average 93.8.

*Juice production*.—13.7 lbs. (~6.2 kg) fruit produces 1 gallon (3.78 L) juice.

*Juice color*.—Strong Red 53B.

*Flavor*.—Fruity, grapey, no labrusca flavor.

*Aroma*.—Sugary, fruity.

*Seed length*.—6.3 mm.

*Seed width*.—4.58 mm.

*Seed thickness*.—3.35 mm.

*Seed shape*.—Pyriform.

*Seed color*.—Dark Greyish Yellow Brown 199B with Strong Yellow Brown 199D mottling.

Cluster:

*Overall shape*.—Pyramidal.

*Relative size*.—Larger than 'Crimson Pearl' and 'Verona' (U.S. Plant Pat. No. 30,631).

*Weight*.—147 g to 269 g; Average 194.3 g.

*Length*.—10 cm to 15.5 cm; Average 12.7 cm.

*Width*.—8.5 cm to 13 cm; Average 11.1 cm.

*Peduncle length*.—7.94 cm to 10.82 cm; Average 8.93 cm.

*Peduncle thickness*.—2.21 mm to 3.1 mm; Average 2.51 mm.

*Pedicel length*.—2.2 mm to 6.7 mm; Average 4.61 mm.

*Pedicel thickness*.—3.63 mm to 5.82 mm; Average 4.64 mm.

*Market use*.—Wine production.

*Storage quality*.—Poor.

*Shipping quality*.—Average.

*Disease resistance/susceptibility*.—High resistance to downy mildew (*Plasmopara viticola*); good resistance to powdery mildew (*Erysiphe necator* (Schw.) Burr.); Good resistance to black rot (*Guignardia bidwellii*), Anthracnose, and trunk diseases.

The invention claimed is:

1. A new and distinct grape plant named 'Resilience' substantially as described and illustrated herein.

* * * * *